(12) United States Patent
Burckhardt et al.

(10) Patent No.: US 11,242,428 B2
(45) Date of Patent: Feb. 8, 2022

(54) HYDROXYALDIMINE AND CURABLE POLYURETHANE COMPOSITION WITH A LOW MONOMERIC ISOCYANATE CONTENT

(71) Applicant: SIKA TECHNOLOGY AG, Baar (CH)

(72) Inventors: Urs Burckhardt, Zürich (CH); Andreas Kramer, Zürich (CH); Martin Schmider, Hamburg (DE)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 15/776,525

(22) PCT Filed: Dec. 20, 2016

(86) PCT No.: PCT/EP2016/081983
§ 371 (c)(1),
(2) Date: May 16, 2018

(87) PCT Pub. No.: WO2017/108829
PCT Pub. Date: Jun. 29, 2017

(65) Prior Publication Data
US 2018/0327535 A1 Nov. 15, 2018

(30) Foreign Application Priority Data
Dec. 21, 2015 (EP) .................................. 15201650

(51) Int. Cl.
| | | |
|---|---|---|
| C07C 251/24 | (2006.01) | |
| C08G 18/32 | (2006.01) | |
| C08G 18/48 | (2006.01) | |
| C08G 18/75 | (2006.01) | |
| C08G 18/10 | (2006.01) | |
| C08G 18/22 | (2006.01) | |
| C09J 175/04 | (2006.01) | |
| C08G 18/76 | (2006.01) | |
| C08G 18/80 | (2006.01) | |
| C08G 18/79 | (2006.01) | |
| C09J 175/08 | (2006.01) | |

(52) U.S. Cl.
CPC ........ *C08G 18/3296* (2013.01); *C07C 251/24* (2013.01); *C08G 18/10* (2013.01); *C08G 18/227* (2013.01); *C08G 18/4825* (2013.01); *C08G 18/4837* (2013.01); *C08G 18/755* (2013.01); *C08G 18/7664* (2013.01); *C08G 18/7671* (2013.01); *C08G 18/792* (2013.01); *C08G 18/8041* (2013.01); *C09J 175/04* (2013.01); *C09J 175/08* (2013.01)

(58) Field of Classification Search
CPC .................................................... C07C 251/24
See application file for complete search history.

(56) References Cited

U.S. PATENT DOCUMENTS

2015/0111991 A1\* 4/2015 Kitamura ........... C08G 59/4007
523/400

FOREIGN PATENT DOCUMENTS

| CN | 101646704 A | 2/2010 |
|---|---|---|
| DE | 25 46 536 A1 | 4/1977 |
| EP | 2 857 378 A1 | 4/2015 |
| WO | 00/64860 A1 | 11/2000 |
| WO | 03/006521 A1 | 1/2003 |
| WO | 2007/036575 A1 | 4/2007 |
| WO | 2008/116927 A1 | 10/2008 |

OTHER PUBLICATIONS

Mar. 22, 2017 International Search Report issued in International Patent Application No. PCT/EP2016/081983.
Jun. 26, 2018 International Preliminary Report on Patentability issued in International Patent Application No. PCT/EP2016/081983.
May 13, 2020 Office Action issued in European Patent Application No. 16 820 246.3.
Jun. 19, 2020 Office Action issued in Chinese Patent Application No. 201680074629.8.

\* cited by examiner

*Primary Examiner* — Michael L Leonard
(74) *Attorney, Agent, or Firm* — Oliff PLC

(57) ABSTRACT

Hydroxyaldimines of formula (I), their reaction products, in particular products of their reaction with polyisocyanates, and compositions including isocyanate groups and containing such reaction products. The hydroxyaldimine permits compositions which have good storage stability, a long open time, low odour, rapid, bubble-free curing and good mechanical properties, and which are not susceptible to plasticizer migration and have a particularly low content of monomeric diisocyanates. In particular, it permits reactive hot-melt adhesives with a particularly good workability.

16 Claims, No Drawings

HYDROXYALDIMINE AND CURABLE POLYURETHANE COMPOSITION WITH A LOW MONOMERIC ISOCYANATE CONTENT

TECHNICAL FIELD

The invention relates to aldimines and polyurethanes, and to adhesives, sealants and coatings.

PRIOR ART

Curable polyurethane compositions which crosslink through reaction of isocyanate groups with hydroxyl groups and/or moisture or water are used in many industrial applications, for example as adhesives, sealants or coatings in the construction and manufacturing industries. The standard products have a considerable content of monomeric isocyanates. This is especially true of two-component systems in which the isocyanate component consists largely of monomeric diisocyanates. But one-component systems based on what are called prepolymers, which are addition products of monomeric diisocyanates with polyols, typically also contain an undesirably high content of monomeric diisocyanates. Since the addition proceeds relatively unselectively and there is chain extension, unreacted monomeric diisocyanates remain in such products. Monomeric diisocyanates are compounds harmful to health, which escape from the products under particular application conditions and can constitute a risk to the user owing to their respiratory tract-irritating or -sensitizing effect and are therefore increasingly undesirable from the point of view of occupational hygiene. This is especially true of spray applications and of compositions that are to be processed while hot, for example hotmelt adhesives.

Various ways of lowering the proportion of monomeric diisocyanates in polyurethane prepolymers or polyurethane compositions have been described. For instance, the monomeric diisocyanates can be physically removed, for example by extraction or distillation, but this is complex and therefore costly. A low NCO/OH ratio in the preparation of the prepolymers likewise leads to a low content of monomeric diisocyanates, but prepolymers prepared in this way, owing to the greater degree of chain extension, have a distinctly elevated viscosity and are thus generally more difficult to process and less storage-stable. The use of asymmetric diisocyanates having two isocyanate groups of different reactivity, as described, for example, in WO 03/006521, likewise leads to a low content of monomeric diisocyanates. But prepolymers of this kind cure slowly since only the less reactive of the two isocyanate groups is available for the crosslinking.

WO 2007/036575 describes a hotmelt polyurethane adhesive having low isocyanate monomer content and a method of reducing the content of monomeric diisocyanates by reacting them with specific long-chain ester aldimines containing a reactive group having active hydrogen. But the aldimines disclosed and the reaction products thereof are thermally sensitive, and the hotmelt adhesives obtained therewith have a limited lifetime when they are being heated. In the typical application of such hotmelt adhesives by means of open rolls, there are therefore soon instances of thickening and hardening on the roll, which lead to a shutdown of the system and can entail complex cleaning.

WO 2008/116927 likewise describes a process for producing a polyurethane composition having low isocyanate monomer content, in which the composition is reacted with a blocked amine containing a reactive group having active hydrogen. But the aldimines described cause intense odor immissions as a result of the volatile blocking agents released, and some of them lead to low storage stabilities and undesirably short open times of the compositions formulated therewith. They are entirely unsuitable for use as hotmelt adhesives which are processed at high temperature typically by means of open rolls exposed to the air.

SUMMARY OF THE INVENTION

It is therefore an object of the present invention to provide a route to curable polyurethanes having a low content of monomeric diisocyanates which overcomes the disadvantages of the prior art.

It has been found that, surprisingly, this object is achieved by a hydroxyaldimine of the formula (I) as described in claim 1. The hydroxyaldimine of the formula (I) is odorless, pH-neutral, liquid and of low viscosity at room temperature, and has low sensitivity to heat and moisture. It can thus be stored, transported, metered and worked in a simple manner.

The hydroxyaldimine of the formula (I) is suitable for preparation of reaction products having aldimino groups, especially in that it is reacted with polyisocyanates with exclusion of moisture. It is possible here to very effectively lower the content of monomeric diisocyanates of polyurethane polymers containing isocyanate groups, which is very advantageous for toxicological reasons. The reaction products obtained are very storage-stable on their own and in compositions containing isocyanate groups. Under the influence of moisture, their aldimino groups react relatively slowly but nevertheless completely and faultlessly, and the reaction can also be speeded up by means of suitable catalysts. This enables a wide range of open times. The aldehyde released in the hydrolysis is nonvolatile, odorless and colorless, and thus does not cause any emissions or odor immissions or discoloration. It has good compatibility in polyurethanes and has barely any tendency to plasticizer migration. This is surprising. Aldimines having elimination products of high molecular weight are naturally particularly critical in relation to plasticizer migration after curing, since the amount used is correspondingly high owing to the high equivalent weight, and hence a large amount of aldehyde released remains in the cured material. Moreover, the long-chain hydrophobic alkyl or alkoxy substituent, especially given branched structure, would be expected to have comparatively poor compatibility in the hydrophilic polymer skeleton of polyurethanes having hydrogen bonds.

The hydroxyaldimine of the formula (I), or reaction products thereof, is particularly suitable for use in reactive polyurethane hotmelt adhesives. It reduces the content of monomeric diisocyanates therein and enables particularly good thermal stabilities. What is particularly surprising is the excellent stability of hotmelt adhesives produced with hydroxyaldimine of the formula (I) in the hot molten state, where no significant increase in viscosity is observed in the processing of such hotmelt adhesives on open rotating rolls over many hours.

The hydroxyaldimine of the formula (I) or reaction products thereof enable polyurethane compositions which have a low content of monomeric diisocyanates, good storage stability and working times that are user-friendly and which crosslink rapidly and completely and without blistering or odor immissions. This gives rise to a blister-free material having a non-tacky surface and good strength, extensibility and durability, which does not have a tendency to problems with plasticizer migration such as bleeding, substrate discoloration or stress-cracking in the substrate.

Further aspects of the invention are the subject of further independent claims. Particularly preferred embodiments of the invention are the subject of the dependent claims.

Ways of Executing the Invention

The invention provides a hydroxyaldimine of the formula (I)

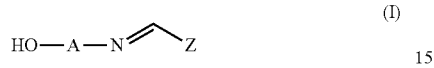

where
Z is an aryl radical substituted by an alkyl or alkoxy group and having a total of
12 to 26 carbon atoms, and
A is a divalent aliphatic or cycloaliphatic or arylaliphatic hydrocarbyl radical optionally containing ether oxygen and having a molecular weight in the range from 28 to 500 g/mol.

A dotted line in the formulae in each case represents the bond between a substituent and the corresponding molecular radical.

A "primary amino group" refers to an amino group which is bonded to a single organic radical and bears two hydrogen atoms; a "secondary amino group" refers to an amino group which is bonded to two organic radicals which may also together be part of a ring and bears one hydrogen atom; and a "tertiary amino group" refers to an amino group which is bonded to three organic radicals, two or three of which may also be part of one or more rings, and does not bear any hydrogen atom.

Substance names beginning with "poly", such as polyamine, polyol or polyisocyanate, refer to substances containing, in a formal sense, two or more of the functional groups that occur in their name per molecule.

A "primary polyamine" refers to a compound having at least two primary amino groups.

An "aromatic isocyanate" refers to an isocyanate wherein the isocyanate groups are bonded directly to an aromatic carbon atom. Accordingly, isocyanate groups of this kind are referred to as "aromatic isocyanate groups". "Molecular weight" refers to the molar mass (in g/mol) of a molecule or a molecule residue. "Average molecular weight" refers to the number-average molecular weight ($M_n$) of a polydisperse mixture of oligomeric or polymeric molecules or molecule residues. It is typically determined by means of gel permeation chromatography (GPC) against polystyrene as standard.

The term "viscosity" refers to the dynamic viscosity or shear viscosity which is defined by the ratio between the shear stress and the shear rate (speed gradient) and is determined as described in DIN EN ISO 3219.

A substance or composition is referred to as "storage-stable" or "storable" when it can be stored at room temperature in a suitable container over a prolonged period, typically over at least 3 months up to 6 months or more, without any change in its application or use properties to a degree of relevance for the use thereof as a result of the storage.

A composition referred to as a "one-component" composition is one in which all ingredients of the composition are in the same container and which is storage-stable per se.

A composition referred to as a "two-component" composition is one in which the ingredients of the composition are in two different components which are stored in separate containers and are not mixed with one another until shortly before or during the application of the composition.

"Curing" or "crosslinking" refers to the chemical setting of a curable composition.

"Room temperature" refers to a temperature of 23° C.

Z is preferably a radical of the formula (II)

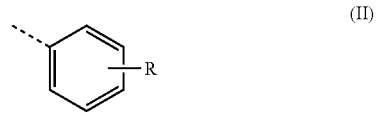

where R is a linear or branched alkyl or alkoxy radical having 6 to 20, preferably 8 to 16, carbon atoms.

R is preferably a linear or branched alkyl radical having 10 to 14 carbon atoms or a linear or branched alkoxy radical having 8 to 12 carbon atoms.

R is especially a linear or branched alkyl radical having 10 to 14 carbon atoms. A hydroxyaldimine of this kind is particularly reactive.

R is more preferably a branched alkyl radical. A hydroxyaldimine of this kind is typically liquid and of comparatively low viscosity at room temperature, which is advantageous for handling thereof.

In particular, R is a branched alkyl radical having 10 to 14 carbon atoms.

R is most preferably a branched alkyl radical having 10 to 14 carbon atoms. A hydroxyaldimine of this kind is particularly reactive and is usually liquid and of comparatively low viscosity at room temperature.

Preferably, R is in the meta or para position, especially in the para position. A hydroxyaldimine of this kind is obtainable particularly readily.

Most preferably, R is a radical of the formula

where $R^1$ and $R^2$ are each an alkyl radical and together have 9 to 13 carbon atoms. Preferably, the $R^1$ and $R^2$ radicals are each linear.

Most preferably, Z is thus a radical of the formula (IIa)

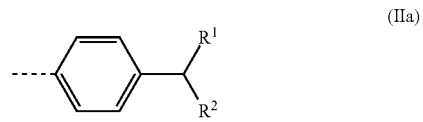

where $R^1$ and $R^2$ have the definitions given.

The preferred Z radicals are obtainable particularly readily and enable particularly low-odor hydroxyaldimines which are especially liquid and particularly of low viscosity at room temperature.

A preferably has a molecular weight in the range from 28 to 250 g/mol.

A is more preferably a radical selected from the group consisting of 1,2-ethylene, 1,2-propylene, 1,3-propylene, 1,5-pentylene, 1,6-hexylene, (1,5,5-trimethylcyclohexan-1-yl)methane-1,3 and 3-oxa-1,5-pentylene.

Among these, preference is given to 1,2-ethylene, 1,5-pentylene, 1,6-hexylene, (1,5,5-trimethylcyclohexan-1-yl) methane-1,3 or 3-oxa-1,5-pentylene. These A radicals are obtainable particularly readily.

Particular preference is given to 3-oxa-1,5-pentylene. These hydroxyaldimines do not have a tendency to cyclize, and enable compositions containing isocyanate groups and having a particularly low content of monomeric diisocyanates and hotmelt adhesives having particularly good stability during processing in the molten state.

Particular preference is further given to (1,5,5-trimethylcyclohexan-1-yl)methane-1,3. These hydroxyaldimines do not have a tendency to cyclize, and enable compositions containing isocyanate groups and having a particularly low content of monomeric diisocyanates and having particularly good storage stability.

The preferred hydroxyaldimines of the formula (I) have particularly good obtainability and enable particularly good properties in the use of the invention.

The hydroxyaldimine of the formula (I) may be in equilibrium with a cyclic compound of the formula (I')

where A and Z have the definitions already given. Compounds of the formula (I') are observed especially in the case that the aldimino group and the hydroxyl group in the hydroxyaldimine of the formula (I) are separated by two or three carbon atoms; in this case they are compound of the formula (I') 2-substituted 1,3-oxazolidines (5-membered ring) or tetrahydro-1,3-oxazines (6-membered ring).

The hydroxyaldimine of the formula (I) is preferably obtained from the reaction of at least one amine of the formula (III) with at least one aldehyde of the formula (IV) in a condensation reaction with release of water.

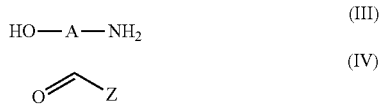

In the formulae (III) and (IV), A and Z have the definitions already given. The aldehyde of the formula (IV) is preferably used here stoichiometrically or in a stoichiometric excess in relation to the primary amino groups. In this manner, the reaction product is largely or entirely free of primary amino groups.

The invention thus further provides a reaction product comprising at least one hydroxyaldimine of the formula (I), obtained from the reaction of at least one amine of the formula (III) with at least one aldehyde of the formula (IV) in a condensation reaction with release of water, wherein the aldehyde was present stoichiometrically or in a stoichiometric excess in relation to the primary amino groups.

The reaction is advantageously conducted at a temperature in the range from 15 to 120° C., preferably at 20 to 100° C., optionally in the presence of a solvent. The water of condensation is preferably removed from the reaction mixture, either as an azeotrope with a suitable solvent or preferably directly by distillation, optionally under reduced pressure.

Optionally, a catalyst is used in the reaction, especially an acid catalyst.

Particular preference is given to working without solvent and removing the water of condensation from the heated reaction mixture by means of application of reduced pressure.

A reaction product of this kind can be used without further workup as hydroxyaldimine of the formula (I).

Preferably, the amine of the formula (III) is combined with the aldehyde of the formula (IV) to give a reaction mixture, where the aldehyde is present stoichiometrically or in a stoichiometric excess in relation to the primary amino groups, and the water of condensation is removed from the reaction mixture by a suitable method, optionally while heating the reaction mixture.

Suitable amines of the formula (III) are primary hydroxylamines, especially 2-aminoethanol, 2-methylaminoethanol (2-amino-1-propanol), 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol, 4-(2-aminoethyl)-2-hydroxyethylbenzene, 3-aminomethyl-3,5,5-trimethylcyclohexanol, a primary amino group-bearing derivative of glycols such as diethylene glycol, dipropylene glycol, dibutylene glycol, or higher oligomers or polymers of these glycols, especially 2-(2-aminoethoxy)ethanol, 2-(2-(2-aminoethoxy)ethoxy)ethanol, α-(2-hydroxymethylethyl)-ω-(2-aminomethylethoxy)poly(oxy(methyl-1,2-ethanediyl)), polyalkoxylated tri- or polyhydric alcohol derivatives that bear one hydroxyl group and one primary amino group, products from the single cyanoethylation and subsequent hydrogenation of glycols, especially 3-(2-hydroxyethoxy)propylamine, 3-(2-(2-hydroxyethoxy)ethoxy)propylamine or 3-(6-hydroxyhexyloxy)propylamine. Preference is given to 2-aminoethanol, 2-methylaminoethanol (2-amino-1-propanol), 1-amino-2-propanol, 3-amino-1-propanol, 5-amino-1-pentanol, 6-amino-1-hexanol, 3-aminomethyl-3,5,5-trimethylcyclohexanol or 2-(2-aminoethoxy)ethanol.

Particular preference is given to 3-aminomethyl-3,5,5-trimethylcyclohexanol or 2-(2-aminoethoxy)ethanol.

A preferred aldehyde of the formula (IV) is an aldehyde of the formula (IVa) where R has the definitions already described.

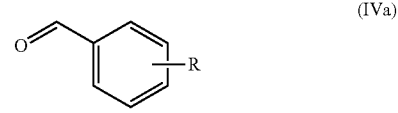

A particularly preferred aldehyde of the formula (IV) is an aldehyde of the formula (IVb) where $R^1$ and $R^2$ have the definitions already described.

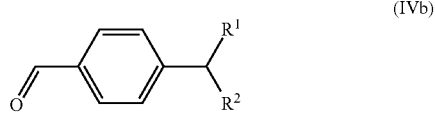

Especially preferred aldehydes of the formula (IV) are 4-decylbenzaldehydes, 4-undecylbenzaldehydes, 4-dodecylbenzaldehydes, 4-tridecylbenzaldehydes or 4-tetradecylbenzaldehydes, in which the alkyl radicals are linear or branched, especially branched.

A most preferred aldehyde of the formula (IV) is a mixture comprising 4-decylbenzaldehydes, 4-undecylbenzaldehydes, 4-dodecylbenzaldehydes, 4-tridecylbenzaldehydes and 4-tetradecylbenzaldehydes, the alkyl radicals of which are mainly branched.

The aldehyde of the formula (IV) is especially obtainable from the formylation of at least one alkyl- and/or alkoxy-substituted aromatic hydrocarbon with carbon monoxide under the action of an acid catalyst. An example of a suitable acid catalyst is the HCl—AlCl$_3$ system (Gattermann-Koch reaction).

In a preferred preparation process, the formylation is conducted with HF—BF$_3$ as acid catalyst. This is advantageous since this process proceeds particularly selectively and the aldehyde of the formula (IV) can be separated from the reaction mixture without a hydrolysis step and the catalyst can be reused, which means that costly and inconvenient product workup and disposal of waste are dispensed with.

The hydroxyaldimine of the formula (I) is preferably selected from the group consisting of N-(4-alkylbenzylidene)-2-aminoethanol, N-(4-alkylbenzylidene)-2-methylaminoethanol, N-(4-alkylbenzylidene)-1-amino-2-propanol, N-(4-alkylbenzylidene)-3-amino-1-propanol, N-(4-alkylbenzylidene)-5-amino-1-pentanol, N-(4-alkylbenzylidene)-6-amino-1-hexanol, N-(4-alkylbenzylidene)-3-aminomethyl-3,5,5-trimethylcyclohexanol and N-(4-alkylbenzylidene)-2-(2-aminoethoxy)ethanol, where alkyl in each case is a linear or particularly branched decyl, undecyl, dodecyl, tridecyl or tetradecyl radical.

Among these, preference is given to N-(4-alkylbenzylidene)-3-aminomethyl-3,5,5-trimethylcyclohexanol or N-(4-alkylbenzylidene)-2-(2-aminoethoxy)ethanol.

Preferably, the hydroxyaldimine of the formula (I) is a mixture of hydroxyaldimines of the formula (I) in which each Z is a radical of the formula (II) and R is selected from alkyl radicals having 6 to 20 carbon atoms. More preferably, R is selected from linear or especially branched decyl, undecyl, dodecyl, tridecyl and tetradecyl radicals.

The invention thus further provides a mixture of hydroxyaldimines of the formula (I) in which each Z is a radical of the formula (II) and R is selected from linear or especially branched decyl, undecyl, dodecyl, tridecyl and tetradecyl radicals.

A mixture of this kind is industrially obtainable particularly easily.

The hydroxyaldimine of the formula (I) may be used as hardener for compositions containing isocyanate groups.

Particularly advantageously, the hydroxyaldimine of the formula (I) is used for preparation of reaction products having aldimino groups, wherein at least one hydroxyaldimine of the formula (I) is reacted with at least one compound having groups reactive toward hydroxyl groups. The compound is preferably polyfunctional in relation to these reactive groups. Particular preference is given to at least one polyisocyanate or at least one polyfunctional ester, especially at least one polyisocyanate. Such reaction products having aldimino groups can advantageously be used as latent hardeners for compositions having isocyanate groups.

It is a feature of the use of the invention that the hydroxyaldimine of the formula (I) or reaction products thereof have excellent compatibility with compositions containing isocyanate groups. They especially enable, with exclusion of moisture, good storage stability together with isocyanate groups and, on contact with moisture, a long open time with rapid and complete curing without causing odor immissions, giving polymers of high mechanical value and stability that do not have a tendency to problems with plasticizer migration.

The invention further provides a reaction product having aldimino groups of the formula (V)

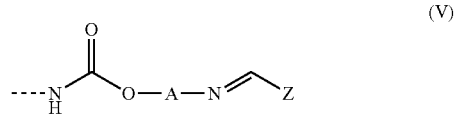

obtained from the reaction of at least one hydroxyaldimine of the formula (I) with at least one polyisocyanate.

In the formula (V), A and Z have the definitions already given.

For the reaction, at least one hydroxyaldimine of the formula (I) is mixed with at least one polyisocyanate with exclusion of moisture, whereupon the hydroxyl groups react with isocyanate groups available. The reaction can be effected at ambient temperature or at an elevated temperature. Preference is given to a temperature in the range from 0 to 180° C., preferably 10 to 180° C., especially 20 to 180° C. A catalyst may be present here, especially a bismuth(III), zinc(II), zirconium(IV) or tin(II) compound or an organotin (IV) compound. In the reaction, it is possible for further ingredients of substances typically used in polyurethane compositions to be present, for example fillers, plasticizers or solvents.

The reaction can be conducted in a substoichiometric manner, i.e. at an OH/NCO ratio below 1. What is obtained here is a reaction product having not only aldimino groups but additionally also isocyanate groups. Such a reaction product is storage-stable with exclusion of moisture. It is especially suitable as latent hardener for compositions containing isocyanate groups or as binder in moisture-curing polyurethane compositions.

In a particularly preferred embodiment, the OH/NCO ratio in the reaction is in the range from 0.05/1 to 0.5/1, especially 0.1/1 to 0.5/1, preferably 0.2/1 to 0.5/1. Such a reaction product crosslinks on contact with moisture to give a solid material. The hydrolyzing aldimino groups react here with isocyanate groups available, and excess isocyanate groups react directly with moisture. If the polyisocyanate is a polyurethane polymer containing isocyanate groups, one advantage of the reaction product is that its content of monomeric diisocyanates is greatly reduced compared to the polyurethane polymer used. At the same time, the reaction product remains usable in the same way as the polyurethane polymer used for the reaction, especially as binder in one-component moisture-curing polyurethanes, without any significant disadvantages in storage stability, reactivity, odor or mechanical properties.

The reaction can also be conducted in a stoichiometric or superstoichiometric manner, i.e. at an OH/NCO ratio of 1 or higher. What is obtained here is a reaction product free of isocyanate groups. Such a reaction product is storage-stable even in the presence of moisture. It is especially suitable as latent hardener in one- or two-component compositions containing isocyanate groups.

In a preferred embodiment, the OH/NCO ratio in the reaction is in the range from 1/1 to 1.5/1, especially 1/1 to 1.2/1, preferably 1/1 to 1.1/1.

Hydroxyaldimines of the formula (I) suitable for the preparation of reaction products having aldimino groups of the formula (V) are those mentioned above, especially the preferred embodiments.

Polyisocyanates suitable for the preparation of reaction products having aldimino groups of the formula (V) are especially
- aliphatic, cycloaliphatic or arylaliphatic di- or triisocyanates, preferably tetramethylene 1,4-diisocyanate, 2-methylpentamethylene 1,5-diisocyanate, hexamethylene 1,6-diisocyanate (HDI), 2,2,4- and/or 2,4,4-trimethylhexamethylene 1,6-diisocyanate (TMDI), decamethylene 1,10-diisocyanate, dodecamethylene 1,12-diisocyanate, lysine diisocyanate or lysine ester diisocyanate, cyclohexane 1,3- or 1,4-diisocyanate, 1-methyl-2,4- and/or -2,6-diisocyanatocyclohexane ($H_6$TDI), 1-isocyanato-3,3,5-trimethyl-5-isocyanatomethylcyclohexane (IPDI), perhydro-2,4'- and/or -4,4'-diphenylmethane diisocyanate ($H_{12}$MDI), 1,3- or 1,4-bis-(isocyanatomethyl)cyclohexane, m- or p-xylylene diisocyanate, tetramethylxylylene 1,3- or 1,4-diisocyanate, 1,3,5-tris(isocyanatomethyl)benzene, bis(1-isocyanato-1-methylethyl)naphthalene, dimer or trimer fatty acid isocyanates such as, in particular, 3,6-bis(9-isocyanatononyl)-4,5-di(1-heptenyl)cyclohexene (dimeryl diisocyanate); especially $H_{12}$MDI or HDI or IPDI;
- aromatic di- or triisocyanates, preferably diphenylmethane 4,4'- or 2,4'- or 2,2'-diisocyanate or any mixtures of these isomers (MDI), tolylene 2,4- or 2,6-diisocyanate or any mixtures of these isomers (TDI), mixtures of MDI and MDI homologs (polymeric MDI or PMDI), phenylene 1,3- or 1,4-diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), tris(4-isocyanatophenyl)methane or tris(4-isocyanatophenyl) thiophosphate; especially MDI or TDI;
- oligomers or derivatives of the di- or triisocyanates mentioned, especially derived from HDI, IPDI, MDI or TDI, especially oligomers containing uretdione or isocyanurate or iminooxadiazinedione groups or various groups among these; or di- or polyfunctional derivatives containing ester or urea or urethane or biuret or allophanate or carbodiimide or uretonimine or oxadiazinetrione groups or various groups among these. In practice, polyisocyanates of this kind are typically mixtures of substances having different degrees of oligomerization and/or chemical structures. They especially have an average NCO functionality of 2.1 to 4.0.
- Polyurethane polymers containing isocyanate groups from the reaction of polyols with the aforementioned polyisocyanates, as described hereinafter.

A suitable polyurethane polymer containing isocyanate groups is especially obtained from the reaction of at least one polyol with a superstoichiometric amount of at least one diisocyanate. The reaction is preferably conducted with exclusion of moisture at a temperature in the range from 50 to 160° C., optionally in the presence of suitable catalysts. The NCO/OH ratio is preferably in the range from 1.3/1 to 2.5/1. The monomeric diisocyanate remaining after the conversion of the OH groups in the reaction mixture can be removed for the most part, especially by means of distillation, which is preferable in the case of a high NCO/OH ratio.

The polyurethane polymer obtained preferably has a content of free isocyanate groups in the range from 0.5% to 10% by weight, especially 1% to 5% by weight, more preferably 1% to 3% by weight. It preferably has a residual content of monomeric diisocyanates in the range from 0.5% to 5% by weight, especially 1% to 3% by weight. The polyurethane polymer can optionally be prepared with additional use of plasticizers or solvents, in which case the plasticizers or solvents used do not contain any groups reactive toward isocyanates.

The polyurethane polymer containing isocyanate groups preferably has an average molecular weight in the range from 500 to 20'000 g/mol, especially 1'000 to 15'000 g/mol, preferably 1'500 to 10'000 g/mol.

Preferred polyisocyanates for preparation of a polyurethane polymer containing isocyanate groups are diisocyanates, especially MDI, TDI, IPDI, HDI or $H_{12}$MDI.

Suitable polyols for preparation of a polyurethane polymer containing isocyanate groups are
- polyether polyols, especially polyoxyalkylenediols and/or polyoxyalkylenetriols, especially polymerization products of ethylene oxide or 1,2-propylene oxide or 1,2- or 2,3-butylene oxide or oxetane or tetrahydrofuran or mixtures thereof, where these may have been polymerized with the aid of a starter molecule having two or more active hydrogen atoms, especially a starter molecule such as water, ammonia or a compound having multiple OH or NH groups, for example 1,2-ethanediol, 1,2- or 1,3-propanediol, neopentyl glycol, diethylene glycol, triethylene glycol, the isomeric dipropylene glycols or tripropylene glycols, the isomeric butanediols, pentanediols, hexanediols, heptanediols, octanediols, nonanediols, decanediols, undecanediols, 1,3- or 1,4-cyclohexanedimethanol, bisphenol A, hydrogenated bisphenol A, 1,1,1-trimethylolethane, 1,1,1-trimethylolpropane, glycerol or aniline, or mixtures of the aforementioned compounds. Likewise suitable are polyether polyols with polymer particles dispersed therein, especially those with styrene-acrylonitrile particles (SAN) or polyurea or polyhydrazodicarbonamide particles (PHD).

Preferred polyether polyols are polyoxypropylenediols or polyoxypropylenetriols, or what are called ethylene oxide-terminated (EO-endcapped) polyoxypropylenediols or -triols. The latter are mixed polyoxyethylene-polyoxypropylene polyols which are especially obtained in that polyoxypropylenediols or -triols, on conclusion of the polypropoxylation reaction, are further alkoxylated with ethylene oxide and hence ultimately have primary hydroxyl groups.

Preferred polyether polyols have a degree of unsaturation of less than 0.02 meq/g, especially less than 0.01 meq/g.
- Polyester polyols, also called oligoesterols, prepared by known processes, especially the polycondensation of hydroxycarboxylic acids or lactones or the polycondensation of aliphatic and/or aromatic polycarboxylic acids with di- or polyhydric alcohols. Preference is given to polyester diols from the reaction of dihydric alcohols, such as, in particular, 1,2-ethanediol, diethylene glycol, 1,2-propanediol, dipropylene glycol, 1,4-butanediol, 1,5-pentanediol, 1,6-hexanediol, neopentyl glycol, glycerol, 1,1,1-trimethylolpropane or mixtures of the aforementioned alcohols, with organic dicarboxylic acids or the anhydrides or esters thereof, such as, in particular, succinic acid, glutaric acid, adipic acid, suberic acid, sebacic acid, dodecanedicarboxylic acid, maleic acid, fumaric acid, phthalic acid, isophthalic acid, terephthalic acid or hexahydrophthalic acid or mixtures of the aforementioned acids, or polyester polyols formed from lactones such as, in particular, ε-caprolactone. Particular preference is given to polyester polyols formed from adipic acid or sebacic acid or dodecanedicarboxylic acid and hexanediol or neopentyl glycol.

Polycarbonate polyols as obtainable by reaction, for example, of the abovementioned alcohols—used to form the polyester polyols—with dialkyl carbonates, diaryl carbonates or phosgene.

Block copolymers bearing at least two hydroxyl groups and having at least two different blocks having polyether, polyester and/or polycarbonate structure of the type described above, especially polyether polyester polyols.

Polyacrylate polyols and polymethacrylate polyols.

Polyhydroxy-functional fats and oils, for example natural fats and oils, especially castor oil; or polyols obtained by chemical modification of natural fats and oils—called oleochemical polyols—for example, the epoxy polyesters or epoxy polyethers obtained by epoxidation of unsaturated oils and subsequent ring opening with carboxylic acids or alcohols, or polyols obtained by hydroformylation and hydrogenation of unsaturated oils; or polyols obtained from natural fats and oils by degradation processes such as alcoholysis or ozonolysis and subsequent chemical linkage, for example by transesterification or dimerization, of the degradation products or derivatives thereof thus obtained. Suitable degradation products of natural fats and oils are especially fatty acids and fatty alcohols, and also fatty acid esters, especially the methyl esters (FAME), which can, for example, be derivatized to hydroxy fatty acid esters by hydroformylation and hydrogenation.

Polyhydrocarbon polyols, also called oligohydrocarbonols, for example polyhydroxy-functional polyolefins, polyisobutylenes, polyisoprenes; polyhydroxy-functional ethylene-propylene, ethylene-butylene or ethylene-propylene-diene copolymers as produced, for example, by Kraton Polymers; polyhydroxy-functional polymers of dienes, especially of 1,3-butadiene, which can especially also be prepared from anionic polymerization; polyhydroxy-functional copolymers of dienes such as 1,3-butadiene or diene mixtures and vinyl monomers such as styrene, acrylonitrile, vinyl chloride, vinyl acetate, vinyl alcohol, isobutylene and isoprene, for example polyhydroxy-functional acrylonitrile/butadiene copolymers as preparable, for example, from epoxides or amino alcohols and carboxyl-terminated acrylonitrile/butadiene copolymers (commercially available, for example, under the Hypro® CTBN or CTBNX or ETBN name from Emerald Performance Materials); and hydrogenated polyhydroxy-functional polymers or copolymers of dienes.

Also especially suitable are mixtures of polyols.

Preference is given to polyether polyols, polyester polyols, polycarbonate polyols, poly(meth)acrylate polyols or polybutadiene polyols.

Particular preference is given to polyether polyols, polyester polyols, especially aliphatic polyester polyols, or polycarbonate polyols, especially aliphatic polycarbonate polyols.

Preference is given to polyols having an average molecular weight in the range from 400 to 20'000 g/mol, preferably from 1'000 to 15'000 g/mol, more preferably 1'500 to 10'000 g/mol, especially 2'000 to 6'000 g/mol.

Preference is given to polyols having an average OH functionality in the range from 1.6 to 4, especially 1.6 to 3.

In the preparation of a polyurethane polymer containing isocyanate groups, it is also possible to use fractions of di- or polyfunctional alcohols, especially 1,2-ethanediol, 1,2-propanediol, 1,3-propanediol, 2-methyl-1,3-propanediol, 1,2-butanediol, 1,3-butanediol, 1,4-butanediol, 1,3-pentanediol, 1,5-pentanediol, 3-methyl-1,5-pentanediol, neopentyl glycol, dibromoneopentyl glycol, 1,2-hexanediol, 1,6-hexanediol, 1,7-heptanediol, 1,2-octanediol, 1,8-octanediol, 2-ethyl-1,3-hexanediol, diethylene glycol, triethylene glycol, dipropylene glycol, tripropylene glycol, 1,3- or 1,4-cyclohexanedimethanol, ethoxylated bisphenol A, propoxylated bisphenol A, cyclohexanediol, hydrogenated bisphenol A, dimer fatty acid alcohols, 1,1,1-trimethylolethane, 1,1,1-trimethylolpropane, glycerol, pentaerythritol, sugar alcohols such as, in particular, xylitol, sorbitol or mannitol, or sugars such as, in particular, sucrose, or alkoxylated derivatives of the alcohols mentioned or mixtures of the alcohols mentioned.

Polyisocyanates preferred for the conversion of reaction products having aldimino groups of the formula (V) are HDI, IPDI, $H_{12}$MDI, TDI, MDI or oligomers or polyurethane polymers of these isocyanates that contain isocyanate groups or mixtures thereof.

Polyurethane polymers containing isocyanate groups that are liquid at room temperature or solid at room temperature are particularly suitable, in the case of which the content of monomeric diisocyanates therein is greatly reduced in the reaction.

A polyurethane polymer containing isocyanate groups which is solid at room temperature may be crystalline, semicrystalline or amorphous at room temperature. A semicrystalline or amorphous polyurethane polymer has only low or zero flowability at room temperature. This means more particularly that it has a viscosity of more than 5'000 Pa·s at 20° C.

The reaction of a hydroxyaldimine of the formula (I) with a polyurethane polymer containing isocyanate groups which is solid at room temperature is preferably effected at a temperature at which the polymer is in molten form, especially at a temperature in the range from 80 to 180° C.

It is likewise possible to prepare a reaction product from a hydroxyaldimine of the formula (I) and a polyurethane polymer containing isocyanate groups, in that the hydroxyaldimine of the formula (I) is added at the early stage of the preparation of the polyurethane polymer containing isocyanate groups.

The reaction product having aldimino groups of the formula (V) especially has the formula (VI)

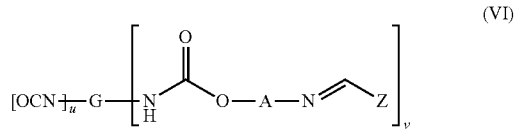

where u is 0 or an integer in the range from 1 to 5 and v is an integer in the range from 1 to 6, where (u+v) is an integer in the range from 2 to 6, G is a (u+v)-valent hydrocarbyl radical which has an average molecular weight in the range from 56 to 20'000 g/mol and optionally contains heteroatoms, and A and Z have the definitions already given.

Preferably, u is 0 or 1 or 2 and v is 1 or 2 or 3 and (u+v) is 2 or 3.

Preferably, G is the radical of one of the preferred polyisocyanates, especially HDI, IPDI, $H_{12}$MDI, TDI, MDI or oligomers or isocyanate-containing polyurethane polymers thereof, after removal of the isocyanate groups.

In a particularly preferred reaction product, G is the radical of a polyurethane polymer containing isocyanate groups after removal of the isocyanate groups and has an average molecular weight in the range from 500 to 20'000 g/mol, especially 1'000 to 15'000 g/mol, preferably 1'500 to 10'000 g/mol, and (u+v) on average has a value in the range from 1.8 to 3, where the average value of u is not less than the average value of v. Such a reaction product on average has at least as many isocyanate groups as aldimino groups. It is especially obtained from the reaction of at least one hydroxyaldimine of the formula (V) with at least one polyurethane polymer containing isocyanate groups in an OH/NCO ratio in the range from 0.05/1 to 0.5/1, especially 0.1/1 to 0.5/1, preferably 0.2/1 to 0.5/1, as described above.

Such a reaction product may also contain proportions of unconverted polyurethane polymer containing isocyanate groups. In such a reaction product, v on average especially has a value in the range from 0.1 to 0.95.

In a further preferred reaction product, G is the radical of a polyurethane polymer containing isocyanate groups after removal of the isocyanate groups and has an average molecular weight in the range from 500 to 20'000 g/mol, especially 1'000 to 15'000 g/mol, preferably 1'500 to 10'000 g/mol, u is 0 and v on average has a value in the range from 1.8 to 3. Such a reaction product is free of isocyanate groups. It is especially obtained from the reaction of at least one hydroxyaldimine of the formula (V) with at least one polyurethane polymer containing isocyanate groups in an OH/NCO ratio in the range from 1/1 to 1.5/1, especially 1/1 to 1.2/1, preferably 1/1 to 1.1/1, as described above. It has the advantageous properties already mentioned.

The reaction products described are particularly suitable for use in compositions containing isocyanate groups, in which case they either themselves contain some or all of the isocyanate groups present therein or may be combined with further polyisocyanates. Both one-component and multicomponent, especially two-component, compositions are possible. The reaction products enable the advantageous properties already mentioned, such as reduced content of monomeric diisocyanates, good storage stability, no odor, long open time, good mechanical properties and barely any tendency to plasticizer migration.

The invention further provides a composition containing isocyanate groups, comprising at least one reaction product having aldimino groups of the formula (V) as described above.

In a preferred embodiment, the composition comprises a reaction product which itself has at least as many isocyanate groups as aldimino groups. This is especially a reaction product which has been obtained from the reaction of at least one hydroxyaldimine of the formula (I) with at least one polyurethane polymer containing isocyanate groups in an OH/NCO ratio in the range from 0.05/1 to 0.5/1, especially 0.1/1 to 0.5/1, preferably 0.2/1 to 0.5/1. Such a composition has the advantage that the content of monomeric diisocyanates is particularly low since a disproportionately large proportion of monomeric diisocyanate has been converted in the reaction with the hydroxyaldimine. Such a composition may additionally contain further polyisocyanates. But it preferably does not contain any further polyisocyanates. It is particularly suitable as a one-component moisture-curing composition. If the reaction product is based on a polyurethane polymer containing isocyanate groups, the composition contains a particularly low content of monomeric diisocyanates. More particularly, it contains a content of monomeric diisocyanates below 1 by weight, preferably below 0.5% by weight, especially below 0.3% by weight. Most preferably, it contains less than 0.1% by weight of monomeric diisocyanates.

In a further preferred embodiment, the composition comprises a reaction product which is itself free of isocyanate groups. Preferably, the reaction product free of isocyanate groups is liquid at room temperature and has an average molecular weight in the range from 56 to 20'000 g/mol, especially 500 to 10'000 g/mol.

In this case, the composition additionally contains at least one polyisocyanate, suitable polyisocyanates being the same as those already mentioned, especially a liquid form of MDI or PMDI or an oligomer of HDI or IPDI or TDI or an isocyanate-containing polyurethane polymer of HDI, IPDI, $H_{12}$MDI, TDI or MDI, or a mixture of the polyisocyanates mentioned. Such a composition is suitable as a one-component or two-component composition.

A one-component composition has the advantage that it is more easily processible.

In the case of a two-component composition, the reaction product having aldimino groups of the formula (V) and the polyisocyanate may be present in the same component or separate components. They are preferably in separate components. Preferably, the reaction product here is based on a polyurethane polymer and the polyisocyanate is a room temperature-liquid form of MDI or PMDI or an oligomer of HDI or IPDI or TDI.

A room temperature-liquid form of MDI is either 4,4'-MDI liquefied by partial chemical modification—especially carbodiimidization or uretonimine formation or adduct formation with polyols—or it is a mixture of 4,4'-MDI with other MDI isomers (2,4'-MDI and/or 2,2'-MDI), and/or with MDI oligomers and/or MDI homologs (PMDI), that has been brought about selectively by blending or results from the production process.

Such a two-component composition has the advantage that the component based on the polyurethane polymer is solely aldimino-functional and hence is not sensitive to contact with moisture provided that it does not come into contact with isocyanate groups. It can therefore be formulated and dispersed with further ingredients in a simple manner. It may be advantageous when a little water is added to such an aldimino-functional component, especially in such an amount that the component contains up to 2% by weight, especially up to 1% by weight, of water. This accelerates the curing.

In the case of a two-component composition, the component separate from the polyisocyanate optionally contains further compounds reactive with isocyanate groups, especially di- or polyfunctional alcohols or polyols or amino alcohols or polyamines or further latent hardeners such as, in particular, ketimines, enamines, oxazolidines, or aldimines that do not conform to the formula (I). Preferably, the two-component composition comprises a polyol, especially having an average molecular weight in the range from 400 to 10'000 g/mol, preferably 500 to 6'000 g/mol, having an average OH functionality in the range from 1.6 to 3, more preferably 1.8 to 3, and having at least partly primary hydroxyl groups, i.e. hydroxyl groups bonded to a $CH_2$ unit, especially a polyether polyol or a polyhydroxy-functional fat or oil. It is especially also possible for a polyether polyol to include polymer particles dispersed therein, especially styrene-acrylonitrile particles (SAN) or acrylonitrile-methyl methacrylate particles.

The two-component composition preferably further comprises at least one di- or polyfunctional alcohol, especially butane-1,4-diol.

Preferably, the composition containing isocyanate groups additionally comprises one or more further ingredients which are especially selected from catalysts, fillers, plasticizers and solvents.

In the case of a two-component composition, such ingredients may be present in just one component or both components.

Suitable catalysts are especially catalysts for the hydrolysis of the aldimino groups, especially organic acids, especially carboxylic acids such as 2-ethylhexanoic acid, lauric acid, stearic acid, isostearic acid, oleic acid, neodecanoic acid, benzoic acid, salicylic acid or 2-nitrobenzoic acid, organic carboxylic anhydrides such as phthalic anhydride, hexahydrophthalic anhydride or methylhexahydrophthalic anhydride, silyl esters of carboxylic acids, organic sulfonic acids such as methanesulfonic acid, p-toluenesulfonic acid or 4-dodecylbenzenesulfonic acid, sulfonic esters, other organic or inorganic acids, or mixtures of the aforementioned acids and acid esters. Particular preference is given to carboxylic acids, especially aromatic carboxylic acids such as benzoic acid, 2-nitrobenzoic acid or especially salicylic acid.

Suitable catalysts are additionally catalysts for the acceleration of the reaction of isocyanate groups, especially organotin(IV) compounds such as, in particular, dibutyltin diacetate, dibutyltin dilaurate, dibutyltin dichloride, dibutyltin diacetylacetonate, dimethyltin dilaurate, dioctyltin diacetate, dioctyltin dilaurate or dioctyltin diacetylacetonate, complexes of bismuth(III) or zirconium(IV), especially with ligands selected from alkoxides, carboxylates, 1,3-diketonates, oxinate, 1,3-ketoesterates and 1,3-ketoamidates, or compounds containing tertiary amino groups, such as, in particular, 2,2'-dimorpholinodiethyl ether (DMDEE).

Also especially suitable are combinations of different catalysts.

Suitable fillers are especially ground or precipitated calcium carbonates, optionally coated with fatty acids, especially stearates, or barytes, quartz flours, quartz sands, dolomites, wollastonites, kaolins, calcined kaolins, sheet silicates such as mica or talc, zeolites, aluminum hydroxides, magnesium hydroxides, silicas including finely divided silicas from pyrolysis processes, cements, gypsums, fly ashes, industrially produced carbon blacks, graphite, metal powders, for example of aluminum, copper, iron, silver or steel, PVC powders or hollow beads.

Suitable plasticizers are especially carboxylic esters such as phthalates, especially diisononyl phthalate (DINP), diisodecyl phthalate (DIDP) or di(2-propylheptyl) phthalate (DPHP), hydrogenated phthalates, especially hydrogenated diisononyl phthalate (DINCH), terephthalates, especially dioctyl terephthalate, trimellitates, adipates, especially dioctyl adipate, azelates, sebacates, benzoates, glycol ethers, glycol esters, organic phosphoric or sulfonic esters, polybutenes, polyisobutenes, or plasticizers derived from natural fats or oils, especially epoxidized soybean oil or linseed oil.

Suitable solvents are especially acetone, methyl ethyl ketone, methyl n-propyl ketone, diisobutyl ketone, methyl isobutyl ketone, methyl n-amyl ketone, methyl isoamyl ketone, acetylacetone, mesityl oxide, cyclohexanone, methylcyclohexanone, ethyl acetate, propyl acetate, butyl acetate, n-butyl propionate, diethyl malonate, 1-methoxy-2-propyl acetate, ethyl 3-ethoxypropionate, diisopropyl ether, diethyl ether, dibutyl ether, diethylene glycol diethyl ether, ethylene glycol diethyl ether, ethylene glycol monopropyl ether, ethylene glycol mono-2-ethylhexyl ether, toluene, xylene, heptane, octane, naphtha, white spirit, petroleum ether or benzine, especially Solvesso™ products (from Exxon), and also methylene chloride, propylene carbonate, butyrolactone, N-methylpyrrolidone or N-ethylpyrrolidone.

The composition may comprise further additives commonly used for polyurethane compositions. More particularly, the following auxiliaries and additives may be present:

nonreactive thermoplastic polymers, especially homo- or copolymers of unsaturated monomers, especially from the group comprising ethylene, propylene, butylene, isobutylene, isoprene, vinyl acetate or alkyl (meth)acrylate, especially polyethylene (PE), polypropylene (PP), polyisobutylene, ethylene-vinyl acetate copolymers (EVA) and atactic poly-α-olefins (APAO); and also polyesters, polyacrylates, polymethacrylates, polyacrylamides, polyacrylonitriles, polyimides, polyamides, polyvinyl chlorides, polysiloxanes, polyurethanes, polystyrenes, and combinations thereof, especially polyetheramide copolymers, styrene-butadiene-styrene copolymers, styrene-isoprene-styrene copolymers, styrene-ethylene-butylene-styrene copolymers, styrene-ethylene-propylene-styrene copolymers; and additionally butyl rubber, polyisobutylene and combinations thereof, and also asphalt, bitumen, raw rubber, fluorinated rubber or cellulose resins;

tackifier resins, especially a hydrocarbon resin such as, in particular, coumarone-indene resins, terpene resins, phenol-modified terpene resins, natural, optionally modified resins such as, in particular, rosin, root resin or tall oil resin, and also a-methylstyrene resins and polymeric lactic acid;

natural resins, fats or oils such as rosin, shellac, linseed oil, castor oil or soya oil;

inorganic or organic pigments, especially titanium dioxide, chromium oxides or iron oxides;

fibers, especially glass fibers, carbon fibers, metal fibers, ceramic fibers, polymer fibers such as polyamide fibers or polyethylene fibers, or natural fibers such as wool, cellulose, hemp or sisal;

dyes;

desiccants, especially molecular sieve powder, calcium oxide, highly reactive isocyanates such as p-tosyl isocyanate, monomeric diisocyanates, monooxazolidines such as Incozol® 2 (from Incorez) or orthoformic esters;

adhesion promoters, especially organoalkoxysilanes, especially epoxysilanes such as, in particular, 3-glycidoxypropyltrimethoxysilane or 3-glycidoxypropyltriethoxysilane, (meth)acrylosilanes, anhydridosilanes, carbamatosilanes, alkylsilanes or iminosilanes, or oligomeric forms of these silanes, or titanates;

latent hardeners or crosslinkers, especially aldimines, ketimines, enamines or oxazolidines;

further catalysts which accelerate the reaction of the isocyanate groups, especially salts, soaps or complexes of tin, zinc, bismuth, iron, aluminum, molybdenum, dioxomolybdenum, titanium, zirconium or potassium, especially tin(II) 2-ethylhexanoate, tin(II) neodecanoate, zinc(II) acetate, zinc(II) 2-ethylhexanoate, zinc(II) laurate, zinc(II) acetylacetonate, aluminum lactate, aluminum oleate, diisopropoxytitanium bis(ethylacetoacetate) or potassium acetate; compounds containing tertiary amino groups, especially N-ethyldiisopropylamine, N,N,N',N'-tetramethylalkylenediamines, pentamethylalkylenetriamines and higher homologs thereof, bis(N,N-diethylaminoethyl) adipate, tris(3-dimethylaminopropyl)amine, 1,4-diazabicyclo[2.2.2]octane (DABCO), 1,8-diazabicyclo[5.4.0]undec-7-ene (DBU), 1,5-diazabicyclo[4.3.0]non-5-ene (DBN), N-alkylmorpholines, N,N'-dimethylpiperazine; aromatic nitrogen compounds such as 4-dimethylaminopyridine, N-methylimidazole, N-vinylimidazole or 1,2-dimethylimidazole; organic ammonium compounds such as benzyltrimethylammonium hydroxide or alkoxylated tertiary amines; what are called "delayed action" catalysts, which are modifications of known metal or amine catalysts;

rheology modifiers, especially thickeners, especially sheet silicates such as bentonites, derivatives of castor oil, hydrogenated castor oil, polyamides, polyamide waxes, polyurethanes, urea compounds, fumed silicas, cellulose ethers or hydrophobically modified polyoxyethylenes;

flame-retardant substances, especially the aluminum hydroxide or magnesium hydroxide fillers already mentioned, and also, in particular, organic phosphoric esters such as, in particular, triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl) phosphate, tris(chloropropyl) phosphate, isopropylated triphenyl phosphate, mono-, bis- or tris(isopropylphenyl) phosphates of different degrees of isopropylation, resorcinol bis(diphenyl phosphate), bisphenol A bis(diphenyl phosphate) or ammonium polyphosphates;

additives, especially wetting agents, leveling agents, defoamers, deaerators, stabilizers against oxidation, heat, light or UV radiation, or biocides;

or further substances customarily used in moisture-curing compositions.

It may be advisable to chemically or physically dry certain substances before mixing them into the composition.

The reaction product having aldimino groups of the formula (V) present in the composition can also be prepared in situ in an otherwise fully formulated composition containing isocyanate groups, in that at least one hydroxyaldimine of the formula (I) is mixed into it with exclusion of moisture and the hydroxyl groups react with isocyanate groups available.

In the composition, the ratio between the groups reactive toward isocyanates, including aldimino groups, and the isocyanate groups is preferably in the range from 0.2 to 1.2, more preferably in the range from 0.4 to 1.0, especially in the range from 0.5 to 0.95.

Preferably, the ratio between aldimino groups and isocyanate groups is in the range from 0.05 to 1.1, more preferably in the range from 0.1 to 1.0, especially in the range from 0.2 to 0.9.

The composition is especially produced with exclusion of moisture, by mixing the constituents of the composition to give a macroscopically homogeneous material, and storing it in moisture-tight containers at ambient temperature. A suitable moisture-tight container especially consists of an optionally coated metal and/or plastic, and is especially a vat, a container, a hobbock, a bucket, a canister, a can, a bag, a tubular bag, a cartridge or a tube.

The composition may take the form of a one-component or of a multi-component, especially two-component, composition.

On application of the composition, the process of crosslinking commences. This results in the cured crosslinked composition.

A one-component composition is applied as such and then begins to cure or to crosslink under the influence of moisture or water. For acceleration of the crosslinking, an accelerator component which contains or releases water and/or a catalyst can be mixed into the composition on application, or the composition can be contacted with such an accelerator component after application thereof.

A two-component composition is applied after the mixing of the two components and begins to crosslink by internal reaction, and the crosslinking may be completed by the action of external moisture.

In the curing or crosslinking, the isocyanate groups react under the influence of moisture with the aldimino groups and any further blocked amino groups present. Some of the isocyanate groups, especially the excess isocyanate groups relative to the aldimino groups, react with one another under the influence of moisture and/or with any further reactive groups present in the composition, especially hydroxyl groups or free amino groups. The totality of these reactions of isocyanate groups that lead to curing of the composition is also referred to as crosslinking.

The moisture required for curing of a one-component composition preferably gets into the composition through diffusion from the air (air humidity). This forms a solid layer of cured composition ("skin") on the surfaces of the composition that are in contact with air. The curing continues in the direction of diffusion from the outside inward, the skin becoming increasingly thick and ultimately encompassing the entire composition applied. The moisture can also get into the composition additionally or entirely from one or more substrate(s) to which the composition has been applied and/or can come from an accelerator component which is mixed into the composition on application or is contacted therewith after application, for example by painting or spraying. Any external humidity required to complete the curing of a two-component composition preferably comes from the air and/or from the substrates.

The composition has a comparatively long open time.

The "open time" refers to the period of time over which the composition can be worked or reworked after the curing process has commenced.

The time until formation of a skin ("skin time" or "tack-free time") is a measure of the open time.

The crosslinking releases an aldehyde of the formula (IV). It is substantially nonvolatile and odorless and remains for the most part in the cured composition. It behaves or acts like a plasticizer therein. As such, it can in principle itself migrate and/or affect the migration of plasticizers. The aldehyde of the formula (IV) has very good compatibility with the cured composition, barely migrates itself, and also does not trigger any enhanced migration of plasticizers.

The composition is preferably an adhesive or a sealant or a coating.

In a preferred embodiment, the adhesive or sealant or coating is elastic and is typically applied at ambient temperature, especially in the range from about 0 to 50° C., preferably in the range from 5 to 40° C.

Such an adhesive and/or sealant may have a pasty consistency with structurally viscous properties and may be applied by means of a suitable device, for example from standard commercial cartridges or vats or hobbocks, for example in the form of a bead, which may have an essentially round or triangular cross-sectional area. But it may also be fluid and only slightly thixotropic and self-leveling.

It is suitable for bonding and sealing applications, especially in the construction and manufacturing industries or in motor-vehicle construction, especially for parquet bonding, installable component bonding, cavity sealing, assembly, module bonding, chassis bonding, glass bonding, join sealing or anchoring.

Elastic bonds in motor-vehicle construction are for example the attachment of parts such as plastic covers, decorative strips, flanges, fenders, drivers' cabins or other installable components to the painted chassis of a motor vehicle, or the bonding of glass panes into the chassis, where the motor vehicles are especially automobiles, trucks, buses, rail vehicles or ships.

The composition is especially suitable as a sealant for the elastic sealing of all kinds of joins, seams or cavities, especially of joins in construction such as dilatation joins or connection joins between components.

An elastic coating may have a fluid consistency and be applied in a self-leveling manner to predominantly flat surfaces, or it may have a certain structural viscosity, such that it does not flow away onto inclined surfaces on application.

As a coating, the composition is especially suitable for protection of buildings or walls, especially for balconies, terraces, open spaces, bridges, parking decks, or for sealing of roofs, especially flat roofs or slightly inclined roof areas or roof gardens, or in the interior of buildings for water sealing, for example beneath tiles or ceramic plates in wet cells or kitchens, or as floorcovering in kitchens, industrial halls or fabrication spaces, or as seal in collection tanks, channels, shafts or wastewater treatment plants, or for protection of surfaces as varnish or seal, or as potting compound for cavity sealing, as seam seal or as protective coating for pipes, for example. It can also be used for repair purposes as seal or coating, for example of leaking roof membranes or floor coverings that are no longer fit for purpose, or more particularly as repair compound for highly reactive spray seals.

In a particularly preferred embodiment, the composition is a reactive hotmelt adhesive (PUR-RHM). In this case, the composition is especially a one-component composition and especially comprises at least one room temperature-solid polyurethane polymer containing isocyanate groups which has been reacted with at least one hydroxyaldimine of the formula (I) in an OH/NCO ratio in the range from 0.05/1 to 0.5/1, especially 0.1/1 to 0.5/1, preferably 0.2/1 to 0.5/1, to give a room temperature-solid reaction product having aldimino groups of the formula (V).

Such a reactive hotmelt adhesive contains a particularly low content of monomeric diisocyanates. This is particularly advantageous for toxicological reasons since the monomeric diisocyanates get into the environment to an increased degree on processing in the hot state and hence are a particularly severe nuisance to the user.

The reactive hotmelt adhesive preferably has a content of room temperature-solid polyurethane polymer including reaction product in the range from 5% to 100% by weight, especially 15% to 95% by weight, more preferably 30% to 90% by weight, most preferably 50% to 80% by weight.

It preferably comprises at least one further polymer selected from the group consisting of nonreactive thermoplastic polymers and tackifier resins.

It preferably has a content of polymers including the room temperature-solid polyurethane polymer including reaction product in the range from 70% to 100% by weight, more preferably 80% to 100% by weight, especially 90% to 100% by weight.

The reactive hotmelt adhesive is melted for application and worked and applied in the molten state. Working is typically effected at a temperature in the range from 80 to 180° C., especially 100 to 180° C. The molten uncrosslinked adhesive should remain stable here in contact with the ambient humidity as a low-viscosity liquid on a rotating roll for a certain time, especially for a few hours, i.e. in particular not exhibit any significant increase in viscosity or any hardening or precipitation. This is possible surprisingly efficiently with the hotmelt adhesive of the invention. After application, the adhesive solidifies very rapidly on cooling, as a result of which it effectively cures immediately and builds up adhesion, but in the uncrosslinked state is still thermoplastic and can be deformed or liquefied again by reheating it. As a result of contact with moisture, the aldimino and isocyanate groups present crosslink as described above, as a result of which the adhesive is additionally chemically crosslinked. A cured crosslinked adhesive is thus obtained, which is not meltable again by reheating to the application temperature.

As a reactive hotmelt adhesive, the composition is especially suitable for construction and industrial applications, especially as lamination adhesive, laminate adhesive, packaging adhesive, textile adhesive or wood adhesive. It is particularly suitable for bonds in which the bonding site is visible, especially for the bonding of glass, for example in motor vehicle and window construction, or for the bonding of see-through packaging.

Suitable substrates which can be bonded or sealed or coated with the composition are especially glass, glass ceramic, concrete, mortar, fiber cement, especially fiber cement boards, brick, tile, gypsum, especially gypsum boards, or natural stone such as granite or marble;

repair or leveling compounds based on PCC (polymer-modified cement mortar) or ECC (epoxy resin-modified cement mortar);

metals or alloys, such as aluminum, copper, iron, steel, nonferrous metals, including surface-finished metals, or alloys such as galvanized or chromed metals;

asphalt or bitumen;

leather, textiles, paper, wood, woodbase materials bonded with resins such as phenolic, melamine or epoxy resins, resin-textile composites or further polymer composites;

plastics such as rigid and flexible PVC, polycarbonate, polystyrene, polyester, polyamide, PMMA, ABS, SAN, epoxy resins, phenolic resins, PUR, POM, TPO, PE, PP, EPM or EPDM, in each case untreated or surface-treated, for example by means of plasma, corona or flames;

fiber-reinforced plastics, such as carbon fiber-reinforced plastics (CFP), glass fiber-reinforced plastics (GFP) and sheet molding compounds (SMC);

insulation foams, especially made of EPS, XPS, PUR, PIR, rockwool, glass wool or foamed glass;

coated or painted substrates, especially painted tiles, coated concrete, powder-coated metals or alloys or painted metal sheets;

paints or varnishes, especially automotive topcoats.

If required, the substrates can be pretreated prior to application, especially by physical and/or chemical cleaning methods or the application of an activator or a primer.

It is possible to bond and/or seal two identical or two different substrates. For bonds with the reactive hotmelt adhesive, preference is given to plastics, textiles, leather, wood, woodbase materials, polymer composites, paper, metals, paints or varnishes, especially with bonding of two different substrates.

The application and curing of the composition affords an article bonded or sealed or coated with the composition. This article may be a built structure or a part thereof, especially a built structure above or below ground, a bridge, a roof, a staircase or a facade, or it may be an industrial good or a consumer good, especially a wood fiber material from the shower and bathroom sector, decorative furniture films, see-through packaging, membrane films comprising textiles such as, in particular, cotton, polyester films in the apparel sector, composites of textiles and foams for automotive finishes, windows, pipes, rotor blades of wind turbines, domestic appliances or a mode of transport such as, in particular, an automobile, a bus, a truck, a rail vehicle, a ship, an aircraft or a helicopter, or an installable component thereof, especially an automobile interior finish component such as, in particular, roof lining, sun visor, dashboard, door panel or parcel shelf.

It is a feature of the composition described that it is particularly storage-stable and may have a particularly low content of monomeric diisocyanates.

On application as an adhesive and/or sealant or coating, it has a comparatively long open time which enables seamless leveling of the material applied or positioning or readjustment of the objects bonded therewith over a prolonged period after application, which is crucial, for example, in the case of coatings over a large area or long sealing strips, or in the case of bonding of large or complex objects.

On application as a reactive hotmelt adhesive, the composition has particularly good stability in contact with the ambient air in the molten state, which means that the adhesive in the hot state can be rotated on an open roll for a few hours without occurrence of a significant increase in viscosity.

The crosslinking of the composition proceeds without blisters, completely and without odor immissions. In the cured state, the composition has good strengths and extensibilities and does not have a tendency to problems with plasticizer migration.

The invention further provides a method of reducing the content of monomeric diisocyanates in a polyurethane polymer containing isocyanate groups by reacting it in a substoichiometric OH/NCO ratio with at least one hydroxyaldimine of the formula (I), with exclusion of moisture, optionally in the presence of catalysts, plasticizers, fillers and/or solvents.

The OH/NCO ratio here is preferably in the range from 0.05/1 to 0.5/1, especially 0.1/1 to 0.5/1, preferably 0.2/1 to 0.5/1.

The polyurethane polymer containing isocyanate groups is especially solid at room temperature and is suitable as a constituent of a reactive hotmelt adhesive.

The products from this method, in addition to the small content of monomeric diisocyanates, have odor-free curing, good storage stability, long open time coupled with rapid curing, and do not have a tendency to problems with plasticizer migration such as bleeding, substrate discoloration or stress cracking in the substrate.

EXAMPLES

Adduced hereinafter are working examples which are intended to elucidate the invention described in detail. It will be appreciated that the invention is not restricted to these described working examples.

Aldehydes Used:
Aldehyde-1: Fractionated reaction mixture obtained from formylation, catalyzed by means of HF—$BF_3$, of $C_{10-14}$-alkylbenzene, containing mainly branched 4-($C_{10-14}$-alkyl)benzaldehydes. (mean aldehyde equivalent weight 290 g/eq)
2,2-Dimethyl-3-lauroyloxypropanal Aldehyde-1 is a mixture of aldehydes of the formula (IV).
2,2-Dimethyl-3-lauroyloxypropanal serves as a comparison.

Preparation of Hydroxyaldimines:
The amine value (including aldimino groups) was determined by means of titration (with 0.1 N $HClO_4$ in acetic acid versus crystal violet).

The viscosity was measured with a thermostated Rheotec RC30 cone-plate viscometer (cone diameter 50 mm, cone angle 1°, cone tip-plate distance 0.05 mm, shear rate 10 $s^{-1}$).

Hydroxyaldimine A1:
25.00 g of aldehyde-1 were initially charged in a round-bottom flask under a nitrogen atmosphere. While stirring, 8.60 g of 2-(2-aminoethoxy)ethanol were added and then the volatile constituents were removed at 80° C. and a reduced pressure at 10 mbar. A pale yellow, odorless and pH-neutral liquid having a viscosity at 20° C. of 0.4 Pa·s and an amine value of 142.9 mg KOH/g was obtained.

Hydroxyaldimine A2:
25.00 g of aldehyde-1 were initially charged in a round-bottom flask under a nitrogen atmosphere. While stirring, 14.02 g of 3-aminomethyl-3,5,5-trimethylcyclohexanol were added and then the volatile constituents were removed at 80° C. and a reduced pressure at 10 mbar. A pale yellow, odorless and pH-neutral liquid having a viscosity at 20° C. of 34.3 Pa·s and an amine value of 122.3 mg KOH/g was obtained.

Hydroxyaldimine R1:
24.46 g of 2,2-dimethyl-3-lauroyloxypropanal were initially charged in a round-bottom flask under a nitrogen atmosphere. While stirring, 8.60 g of 2-(2-aminoethoxy)ethanol were added and then the volatile constituents were removed at 80° C. and a reduced pressure at 10 mbar. An almost colorless, odorless liquid having an amine value of 144.3 mg KOH/g was obtained.

Hydroxyaldimine R2:
24.46 g of 2,2-dimethyl-3-lauroyloxypropanal were initially charged in a round-bottom flask under a nitrogen atmosphere. While stirring, 14.02 g of 3-aminomethyl-3,5,5-trimethylcyclohexanol were added and then the volatile constituents were removed at 80° C. and a reduced pressure at 10 mbar. A pale yellow, odorless liquid having an amine value of 124.2 mg KOH/g was obtained.

The hydroxyaldimines A1 and A2 are hydroxyaldimines of the formula (I) and are inventive examples. The hydroxyaldimines R1 and R2 are comparative examples.

Preparation of Polymers Containing Isocyanate Groups
Polymer P1:
4000 g of polyoxypropylenediol (Acclaim® 4200, from Covestro; OH number 28.5 mg KOH/g) and 520 g of diphenylmethane 4,4'-diisocyanate (Desmodur® 44 MC L, from Covestro) were reacted by a known method at 80° C. to give an NCO-terminated polyurethane polymer which is liquid at room temperature and has a content of free isocyanate groups of 1.85% by weight.

Polymer P2:
300.0 g of polyoxypropylenepolyoxyethylenediol (Desmophen® L300, from Covestro; OH number 190.0 mg KOH/g) and 228.8 g of isophorone diisocyanate (Vestanat® IPDI, Degussa) were reacted by a known method at 60° C.

to give an NCO-terminated polyurethane polymer which is liquid at room temperature and has a content of free isocyanate groups of 8.35% by weight.

Preparation of Reaction Products of the Hydroxyaldimines:

Reaction Product U1:

227.30 g (about 100 mmol NCO) of polymer P1, 9.41 g (about 24 mmol) of hydroxyaldimine A1 and 0.13 g of Coscat® 83 (Bi(III) neodecanoate, from Vertellus) were stirred in a planetary mixer under reduced pressure at 70° C. for 90 minutes. A clear reaction product which is liquid at room temperature and has aldimino and isocyanate groups was obtained.

Reaction Product U2:

227.30 g (about 100 mmol NCO) of polymer P1, 11.02 g (about 24 mmol) of hydroxyaldimine A2 and 0.13 g of Coscat® 83 were stirred in a planetary mixer under reduced pressure at 70° C. for 90 minutes. A clear reaction product which is liquid at room temperature and has aldimino and isocyanate groups was obtained.

Reaction Product U3:

227.30 g (about 100 mmol NCO) of polymer P1, 18.82 g (about 48 mmol) of hydroxyaldimine A1 and 0.13 g of Coscat® 83 were stirred in a planetary mixer under reduced pressure at 70° C. for 90 minutes. A clear reaction product which is liquid at room temperature and has aldimino and isocyanate groups was obtained.

Reaction Product U4:

227.30 g (about 100 mmol NCO) of polymer P1, 22.05 g (about 48 mmol) of hydroxyaldimine A2 and 0.13 g of Coscat® 83 were stirred in a planetary mixer under reduced pressure at 70° C. for 90 minutes. A clear reaction product which is liquid at room temperature and has aldimino and isocyanate groups was obtained.

Reaction Product U5:

227.30 g (about 100 mmol NCO) of polymer P1, 39.61 g (about 101 mmol) of hydroxyaldimine A1 and 0.13 g of Coscat® 83 were stirred in a planetary mixer under reduced pressure at 70° C. for 90 minutes. A clear reaction product which is liquid at room temperature and has aldimino groups and was free of isocyanate groups was obtained.

Reaction Product U6:

227.30 g (about 100 mmol NCO) of polymer P1, 46.42 g (about 101 mmol) of hydroxyaldimine A2 and 0.13 g of Coscat® 83 were stirred in a planetary mixer under reduced pressure at 70° C. for 90 minutes. A clear reaction product which is liquid at room temperature and has aldimino groups and was free of isocyanate groups was obtained.

Reaction Product U7:

60.00 g (about 115 mmol NCO) of polymer P3, 15.82 g (about 40.4 mmol) of hydroxyaldimine A1 and 0.05 g of Coscat® 83 were mixed in a honey jar under argon and then left to react in an air circulation oven at 60° C. for 16 hours. A clear reaction product which is liquid at room temperature and has aldimino and isocyanate groups was obtained.

Reaction Product U8:

60.00 g (about 115 mmol NCO) of polymer P3, 18.51 g (about 40.4 mmol) of hydroxyaldimine A2 and 0.05 g of Coscat® 83 were mixed in a honey jar under argon and then left to react in an air circulation oven at 60° C. for 16 hours. A clear reaction product which is liquid at room temperature and has aldimino and isocyanate groups was obtained.

Reaction Product Q1:

227.30 g (about 100 mmol NCO) of polymer P1, 9.33 g (about 24 mmol) of hydroxyaldimine R1 and 0.13 g of Coscat® 83 were stirred in a planetary mixer under reduced pressure at 70° C. for 90 minutes. A clear reaction product which is liquid at room temperature and has aldimino and isocyanate groups was obtained.

Reaction product Q2:

227.30 g (about 100 mmol NCO) of polymer P1, 10.84 g (about 24 mmol) of hydroxyaldimine R2 and 0.13 g of Coscat® 83 were stirred in a planetary mixer under reduced pressure at 70° C. for 90 minutes. A clear reaction product which is liquid at room temperature and has aldimino and isocyanate groups was obtained.

Reaction Product Q3:

227.30 g (about 100 mmol NCO) of polymer P1, 18.66 g (about 48 mmol) of hydroxyaldimine R1 and 0.13 g of Coscat® 83 were stirred in a planetary mixer under reduced pressure at 70° C. for 90 minutes. A clear reaction product which is liquid at room temperature and has aldimino and isocyanate groups was obtained.

Reaction Product Q4:

227.30 g (about 100 mmol NCO) of polymer P1, 21.68 g (about 48 mmol) of hydroxyaldimine R2 and 0.13 g of Coscat® 83 were stirred in a planetary mixer under reduced pressure at 70° C. for 90 minutes. A clear reaction product which is liquid at room temperature and has aldimino and isocyanate groups was obtained.

Reaction Product Q5:

227.30 g (about 100 mmol NCO) of polymer P1, 39.26 g (about 101 mmol) of hydroxyaldimine R1 and 0.13 g of Coscat® 83 were stirred in a planetary mixer under reduced pressure at 70° C. for 90 minutes. A clear reaction product which is liquid at room temperature and has aldimino groups and was free of isocyanate groups was obtained.

Reaction Product Q6:

227.30 g (about 100 mmol NCO) of polymer P1, 45.62 g (about 101 mmol) of hydroxyaldimine R2 and 0.13 g of Coscat® 83 were stirred in a planetary mixer under reduced pressure at 70° C. for 90 minutes. A clear reaction product which is liquid at room temperature and has aldimino groups and was free of isocyanate groups was obtained.

Reaction Product Q7:

60.00 g (about 115 mmol NCO) of polymer P3, 15.69 g (about 40.4 mmol) of hydroxyaldimine R1 and 0.05 g of Coscat® 83 were mixed in a honey jar under argon and then left to react in an air circulation oven at 60° C. for 16 hours. A clear reaction product which is liquid at room temperature and has aldimino and isocyanate groups was obtained.

The reaction products U1 to U8 are reaction products having aldimino groups of the formula (V) and are inventive examples. The reaction products Q1 to Q7 are comparative examples.

Content of Monomeric Diisocyanates 14 days after production, the content of monomeric 4,4'-MDI in polymer P1 and in some reaction products thereof was determined by means of HPLC (detection via photodiode array; 0.04 M sodium acetate/acetonitrile as mobile phase). The results are reported in table 1.

TABLE 1

|  | 4,4'-MDI content |
| --- | --- |
| Polymer P1 | 2.52% by weight |
| Reaction product U1 | 0.99% by weight |
| Reaction product U3 | 0.35% by weight |
| Reaction product Q1 | 1.88% by weight |
| Reaction product Q3 | 0.20% by weight |

One-Component Compositions
Compositions Z1 to Z3 and Ref1 to Ref3

For each composition, the ingredients specified in table 2 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture. Each composition was tested as follows:

As a measure of storage stability, the Viscosity (1d RT) was determined the day after production, and the Viscosity (7d 60° C.) after storage in a closed container in an air circulation oven at 60° C. for 7 days. The viscosity was measured, at a temperature of 20° C. in each case, with a thermostated Rheotec RC30 cone-plate viscometer (cone diameter 50 mm, cone angle 1°, cone tip-plate distance 0.05 mm, shear rate 10 s$^{-1}$).

As a measure of the open time, the Tack-free time was determined. For this purpose, a few grams of the composition were applied to cardboard in a layer thickness of about 2 mm and, under standard climatic conditions, the time until, when the surface of the composition was gently tapped by means of an LDPE pipette, there were for the first time no residues remaining any longer on the pipette was determined.

To determine the mechanical properties, each composition was poured onto a PTFE-coated film to give a film of thickness 2 mm and stored under standard climatic conditions for 7 days, and a few dumbbells having a length of 75 mm with a bar length of 30 mm and a bar width of 4 mm were punched out of the film and these were tested in accordance with DIN EN 53504 at a strain rate of 200 mm/minute for Tensile strength (breaking force), Elongation at break, Modulus of elasticity 5% (at 0.5-5% elongation) and Modulus of elasticity 50% (at 0.5-50% elongation).

Appearance was assessed visually on the films produced. "Nice" was used to describe a clear film with a nontacky surface without blisters.

Odor was assessed by smelling by nose at a distance of 2 cm from the freshly produced films. "No" means that no odor was perceptible.

The results are reported in table 2.

Compositions Z1 to Z3 are inventive examples. Compositions Ref1 to Ref3 are comparative examples.

TABLE 2

Composition (in parts by weight) and properties of Z1 to Z3 and Ref1 to Ref3.

| Composition | Z1 | Ref1 | Z2 | Ref2 | Z3 | Ref3 |
|---|---|---|---|---|---|---|
| Reaction product | U1 | Q1 | U2 | Q2 | U4 | Q4 |
| | 80.00 | 80.00 | 80.00 | 80.00 | 80.00 | 80.00 |
| Salicylic acid solution[1] | 1.50 | 0.50 | 1.50 | 0.50 | 1.50 | 0.50 |
| Viscosity (1 d RT) | 201 | 77 | 73 | 82 | 121 | 137 |
| [Pa · s] (7 d 60° C.) | 371 | 94 | 98 | 104 | 148 | 180 |
| Tack-free time | 195' | 400' | 165' | 195' | 45' | 45' |
| Tensile strength [MPa] | 3.41 | 5.51 | 1.16 | 0.60 | 0.57 | 0.69 |
| Elongation at break [%] | 946 | >1200 | >1200 | 494 | >1200 | >1200 |
| Modulus of elasticity 5% [MPa] | 1.33 | 1.32 | 0.85 | 0.91 | 0.76 | 0.58 |
| Modulus of elasticity 50% | 0.70 | 0.67 | 0.48 | 0.53 | 0.39 | 0.28 |
| Appearance | nice | nice | nice | nice | nice | nice |
| Odor | no | no | no | no | no | no |

[1]5% in dioctyl adipate

Compositions Z4 and Z5 and Ref4

For each composition, the ingredients specified in table 3 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture. Each composition was tested as follows:

As a measure of plasticizer migration, each composition was applied to a cardboard underlayer such that it had a round base area of diameter 12 mm and a height of 20 mm, and was stored under standard climatic conditions for 7 days. Around each composition, thereafter, a dark oval speck had formed on the cardboard. The dimensions thereof (height and width) were measured and reported in table 3 as Migration.

Compositions Z4 and Z5 are inventive examples. Composition Ref4 is a comparative example.

TABLE 3

Composition (in parts by weight) and properties of Z4 and Z5 and Ref4.

|  |  | Composition | | |
|---|---|---|---|---|
|  |  | Z4 | Z5 | Ref4 |
| Reaction product |  | U7 | U8 | Q7 |
|  |  | 25.0 | 25.0 | 25.0 |
| Chalk[1] |  | 25.0 | 25.0 | 25.0 |
| Silica[2] |  | 1.9 | 1.9 | 1.9 |
| Dibutyltin dilaurate[3] |  | 2.5 | 2.5 | 2.5 |
| Salicylic acid[4] |  | 5.0 | 5.0 | 5.0 |
| Migration | Height | 1 | 1 | 8 |
| [mm] | Width | 1 | 1 | 6 |

[1]ground calcium carbonate coated with fatty acid
[2]hydrophobically modified fumed silica
[3]5% in diisodecyl phthalate
[4]5% in dioctyl adipate Two-Component Compositions Compositions Z6 and Z7 and Ref5 and Ref6

For each composition, the ingredients specified in table 4 were mixed in the specified amounts (in parts by weight) of the first component K1 by means of a centrifugal mixer (SpeedMixer™ DAC 150, FlackTek Inc.) and stored with exclusion of moisture.

As the second component K2, Desmodur® N 3300 (HDI trimer having an NCO content of 21.8% by weight, from Covestro) was used in the amount specified in table 4 (in parts by weight).

Subsequently, the two components of each composition were processed by means of centrifugal mixer to give a homogeneous liquid and this was tested immediately as described for the composition Z1.

The results are reported in table 4.

Compositions Z6 and Z7 are inventive examples. Compositions Ref5 and Ref6 are comparative examples.

TABLE 4

Composition (in parts by weight) and properties of Z6 and Z7 and Ref5 and Ref6.

|  | Composition | | | |
|---|---|---|---|---|
|  | Z6 | Ref5 | Z7 | Ref6 |
| Component K1: |  |  |  |  |
| Reaction product | U5 | Q5 | U6 | Q6 |
|  | 75.00 | 75.00 | 75.00 | 75.00 |
| Salicylic acid solution[1] | 1.50 | 0.50 | 1.50 | 0.50 |
| Component K2: |  |  |  |  |
| Desmodur ® N 3300 | 6.83 | 6.79 | 6.67 | 6.74 |
| Tack-free time | 55' | 45' | 70' | 70' |
| Tensile strength [MPa] | 1.60 | 1.80 | 1.66 | 1.88 |
| Elongation at break [%] | 127 | 150 | 161 | 202 |
| Modulus of elasticity 5% [MPa] | 2.29 | 2.32 | 1.15 | 0.72 |
| Modulus of elasticity 50% [MPa] | 1.53 | 1.51 | 0.85 | 0.54 |
| Appearance | nice | nice | nice | nice |
| Odor | no | no | no | no |

[1]5% in dioctyl adipate

Reactive Hotmelt Adhesives

Adhesives H1 and HR1 and HR2:

A mixture of 30.6 g of polyoxypropylenediol (OH number 56.0 mg KOH/g), 7.2 g of polyoxypropylenediol (OH number 112.5.0 mg KOH/g) and 23.4 g of room temperature-solid acrylate polymer (copolymer of methyl methacrylate and n-butyl methacrylate) was heated up to 140° C. under reduced pressure with stirring until the acrylate polymer had completely dissolved. Then 18.0 g of room temperature-crystalline, linear polyester diol (formed from hexanediol and adipic acid; OH number 28.0 mg KOH/g) were added and the mixture was stirred at 140° C. under reduced pressure for 1 h. Subsequently, 13.6 g of diphenylmethane 4,4'-diisocyanate (Desmodur® 44 MC L, from Covestro) were added and the mixture was stirred at 140° C. under reduced pressure for 30 minutes. Then either 7.2 g of hydroxyaldimine A1 (adhesive H1) or 7.2 g of hydroxy-aldimine R1 (adhesive HR1) or neither (adhesive HR2) were added and the mixture was stirred at 140° C. under reduced pressure for a further 30 minutes, before being cooled and stored with exclusion of moisture.

Each adhesive was tested as follows:

4,4'-MDI content was determined by means of HPLC (detection via photodiode array; 0.04 M sodium acetate/acetonitrile as mobile phase).

Viscosity was determined the day after production by Brookfield Thermosel at 5 rpm with spindle 27 at the specified temperature and referred to as "Viscosity (fresh)".

In the determination of the early strength and mechanical properties, the respective hotmelt adhesive was applied at 150° C. to silicone paper and left to cool, so as to form a film of thickness 500 μm. Test specimens of 20×100 mm were cut out of this and stored under standard climatic conditions. After 30 min, Tensile strength (measure of early strength) was determined for a first time, then again the tensile strength and Elongation at break after 14 days, each in accordance with DIN EN 53504 at a strain rate of 10 mm/min.

To determine Thermal stability in the molten state with ambient humidity, the adhesive was left to rotate under standard climatic conditions on an open roll at a temperature of 140° C. Viscosity was measured at regular intervals (Brookfield Thermosel, 5 rpm, spindle 27).

The results are reported in table 5.

Adhesive H1 is an inventive example. Adhesives HR1 and HR2 are comparative examples.

TABLE 5

Properties of adhesives H1, HR1 and HR2.

| | Adhesive | | |
|---|---|---|---|
| | H1 | HR1 | HR2 |
| Hydroxyaldimine added | A1 | R1 | — |
| 4,4'-MDI content | 0.28% by weight | 0.12% by weight | 1.90% by weight |
| Viscosity (fresh) at 140° C. | 0.3 Pa · s | 3.5 Pa · s | 0.5 Pa · s |
| Tensile strength (after 30') | 0.35 MPa | 0.61 MPa | <0.3 MPa |
| Tensile strength (after 14 d) | 6.9 MPa | 6.0 MPa | n.d.* |
| Elongation at break (after 14 d) | 590% | 530% | n.d.* |
| Viscosity (140° C.) after | | | |
| 0.5 h | 0.3 Pa · s | 3.7 Pa · s | 0.5 Pa · s |
| 1.0 h | 0.3 Pa · s | 4.4 Pa · s | n.d. |
| 1.5 h | 0.3 Pa · s | 6.8 Pa · s | n.d. |
| 2.0 h | 0.3 Pa · s | 7.1 Pa · s | n.d. |
| 2.5 h | 0.3 Pa · s | 7.6 Pa · s | n.d. |
| 3.0 h | 0.3 Pa · s | 8.0 Pa · s | n.d. |
| 3.5 h | 0.3 Pa · s | 12.4 Pa · s | n.d. |
| 4.0 h | 0.3 Pa · s | 16.6 Pa · s | n.d. |
| 4.5 h | 0.3 Pa · s | 24.7 Pa · s | 0.6 Pa · s |
| 5.0 h | 0.3 Pa · s | n.m. | n.d. |
| 8.0 h | 0.3 Pa · s | n.m. | n.d. |
| 9.0 h | 0.3 Pa · s | n.m. | n.d. |
| 10.0 h | 2.0 Pa · s | n.m. | n.d. |
| 12.0 h | 4.7 Pa · s | n.m. | n.d. |
| 14.0 h | 5.4 Pa · s | n.m. | n.d. |
| 16.0 h | 4.8 Pa · s | n.m. | 2.2 Pa · s |

"n.m." means "not measurable" (viscosity too high/gelated).
"n.d." means "not measured".
*blisters in the film

The invention claimed is:

1. A hydroxyaldimine of the formula (I)

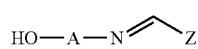

(I)

wherein

A is a divalent aliphatic or cycloaliphatic or arylaliphatic hydrocarbyl radical optionally containing ether oxygen and having a molecular weight in a range of from 28 to 500 g/mol, and Z is a radical of the formula (II):

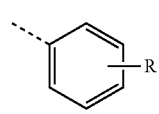

(II)

where

R is a radical of the formula

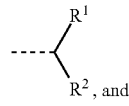

$R^1$ and $R^2$ are each an alkyl radical and together have 9 to 13 carbon atoms.

2. The hydroxyaldimine as claimed in claim 1, wherein A is selected from the group consisting of 1,2-ethylene, 1,2-propylene, 1,3-propylene, 1,5-pentylene, 1,6-hexylene, (1,5,5-trimethylcyclohexan-1-yl)methane-1,3 , and 3-oxa-1,5-pentylene.

3. A reaction product containing at least one of the hydroxyaldimine as claimed in claim 1, obtained from a reaction of at least one amine of the formula (III) with at least one aldehyde of the formula (IV) in a condensation reaction with release of water, wherein the at least one aldehyde was present stoichiometrically or in a stoichiometric excess in relation to the primary amino groups, and the formulae (III) and (IV) are:

(III)

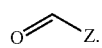

(IV)

4. A mixture including two or more of the hydroxyaldimines as claimed in claim 1, wherein R is selected from the group consisting of branched decyl, undecyl, dodecyl, tridecyl, and tetradecyl radicals.

5. A reaction product having aldimino groups of the formula (V)

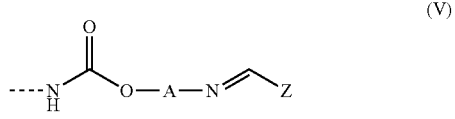

(V)

obtained from a reaction of at least one of the hydroxyaldimine as claimed in claim 1 with at least one polyisocyanate.

6. The reaction product as claimed in claim 5, further comprising isocyanate groups, and an OH/NCO ratio in the reaction is in a range of from 0.05/1 to 0.5/1.

7. The reaction product as claimed in claim 5, wherein the reaction product is free of isocyanate groups and an OH/NCO ratio in the reaction is in a range of from 1/1 to 1.5/1.

8. A composition containing isocyanate groups, comprising at least one of the reaction product as claimed in claim 5.

9. The composition as claimed in claim 8, further comprising at least one ingredient selected from the group consisting of catalysts, fillers, plasticizers, and solvents.

10. The composition as claimed in claim 8, wherein the composition is an adhesive or a sealant or a coating.

11. The composition as claimed in claim 10, wherein the composition is a reactive hotmelt adhesive.

12. A method of reducing content of monomeric diisocyanates in a polyurethane polymer containing isocyanate groups by reacting it in a substoichiometric OH/NCO ratio with at least one of the hydroxyaldimine as claimed in claim 1, with exclusion of moisture.

13. The hydroxyaldimine as claimed in claim 1, wherein A is 3-oxa-1,5-pentylene or (1,5,5-trimethylcyclohexan-l-yl)methane-1,3.

14. The hydroxyaldimine as claimed in claim 1, wherein A is (1,5,5-trimethylcyclohexan-l-yl)methane-1,3.

15. The mixture as claimed in claim 4, wherein A is 3-oxa-1,5-pentylene or (1,5,5-trimethylcyclohexan-l-yl)methane-1,3.

16. The mixture as claimed in claim 4, wherein A is (1,5,5-trimethylcyclohexan-l-yl)methane-1,3.

* * * * *